(12) United States Patent
Schluter

(10) Patent No.: US 7,510,686 B2
(45) Date of Patent: Mar. 31, 2009

(54) SAMPLE CYLINDER, ESPECIALLY A SAMPLE CYLINDER THAT IS PROVIDED WITH A FILTRATION DEVICE FOR RECOVERING CELL MATERIAL FROM BODY FLUIDS

(76) Inventor: Gert Schluter, Grubenfeldstrasse 18, Endingen (DE) 79346

( * ) Notice: Subject to any disclaimer, the term of this patent is extended or adjusted under 35 U.S.C. 154(b) by 222 days.

(21) Appl. No.: 10/275,781

(22) PCT Filed: May 16, 2001

(86) PCT No.: PCT/DE01/01839

§ 371 (c)(1),
(2), (4) Date: Nov. 8, 2002

(87) PCT Pub. No.: WO01/88501

PCT Pub. Date: Nov. 22, 2001

(65) Prior Publication Data

US 2003/0175166 A1 Sep. 18, 2003

(30) Foreign Application Priority Data

May 18, 2000 (DE) ............................... 100 24 137

(51) Int. Cl.
*B01L 11/00* (2006.01)
(52) U.S. Cl. ....................... 422/101; 422/100; 422/102; 436/174; 436/177; 436/178

(58) Field of Classification Search ................... 422/61, 422/68.1, 99, 100, 101, 102; 436/174, 177, 436/178, 179; 604/1, 2, 3; 73/864.01, 864.13, 73/864.31
See application file for complete search history.

(56) References Cited

U.S. PATENT DOCUMENTS 3,008,570 A * 11/1961 Roehr et al. ................. 206/229
4,174,238 A * 11/1979 Fowles et al. ................. 156/69

(Continued)

FOREIGN PATENT DOCUMENTS

DE 298 06 021 8/1998

(Continued)

*Primary Examiner*—Dwayne K. Handy
(74) *Attorney, Agent, or Firm*—Cohen Pontani Lieberman & Pavane LLP

(57) ABSTRACT

For the purpose of obtaining medical preparations by means of a printing technique, a specimen cylinder is provided with a syringe cone segment that can be separated from a cylinder segment. After the syringe cone segment has been removed, a filtering device with a filter which is held so as to be sealed relative to the inner wall of the specimen cylinder projects beyond its holder and beyond the cylinder segment in an operational position of the filtering device and can be pressed onto a specimen carrier in a simple manner.

11 Claims, 3 Drawing Sheets

U.S. PATENT DOCUMENTS

| | | | | |
|---|---|---|---|---|
| 4,595,021 A | * | 6/1986 | Shimizu et al. | 600/578 |
| 4,806,313 A | * | 2/1989 | Ebersole et al. | 422/61 |
| 4,961,432 A | * | 10/1990 | Guirguis | 600/573 |
| 4,973,450 A | | 11/1990 | Schlüter | 422/101 |
| 5,079,170 A | * | 1/1992 | Rosman et al. | 436/178 |
| 5,083,793 A | * | 1/1992 | Sanford | 273/249 |
| 5,093,263 A | * | 3/1992 | Marlar et al. | 436/18 |
| 5,266,266 A | * | 11/1993 | Nason | 422/58 |
| 5,322,800 A | * | 6/1994 | Murphy | 436/176 |
| 5,352,410 A | * | 10/1994 | Hansen et al. | 422/58 |
| 5,888,831 A | * | 3/1999 | Gautsch | 436/177 |
| 5,919,356 A | * | 7/1999 | Hood | 210/85 |
| 6,129,894 A | * | 10/2000 | Rabenecker et al. | 422/61 |
| 6,719,733 B1 | * | 4/2004 | Heffernan et al. | 604/199 |

FOREIGN PATENT DOCUMENTS

WO     00 20092     4/2000

* cited by examiner

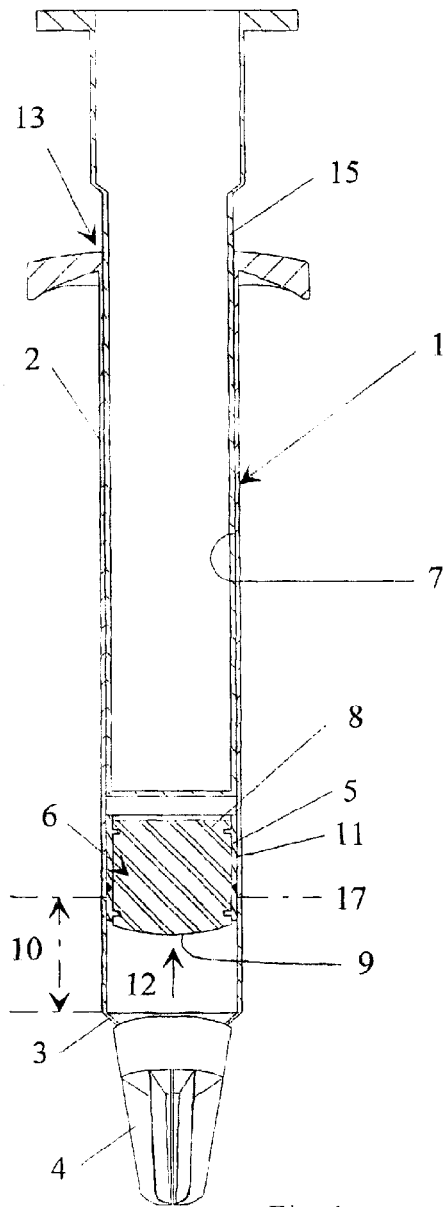
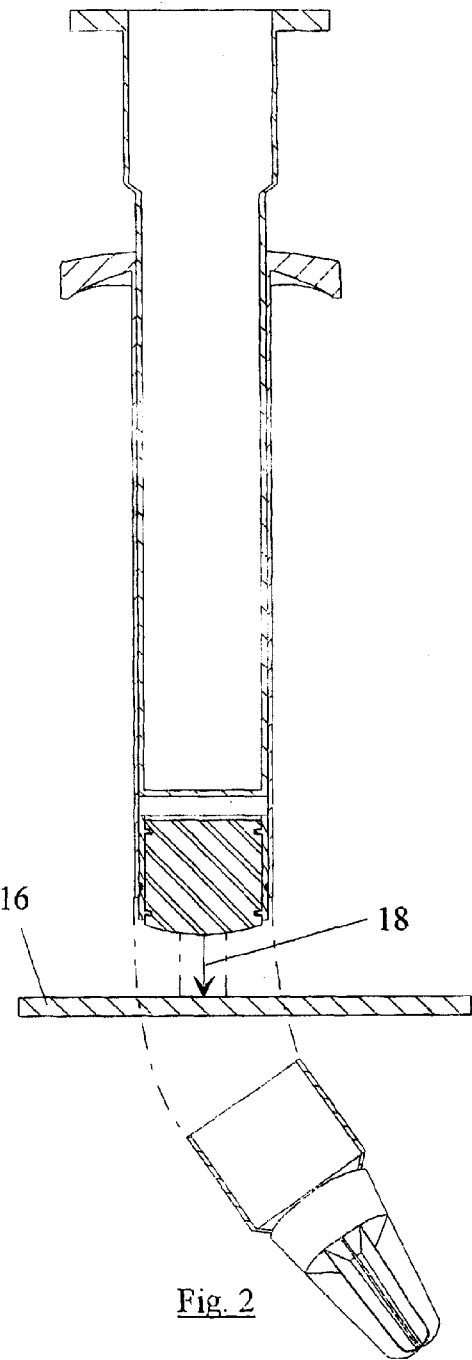
Fig. 1
Fig. 2

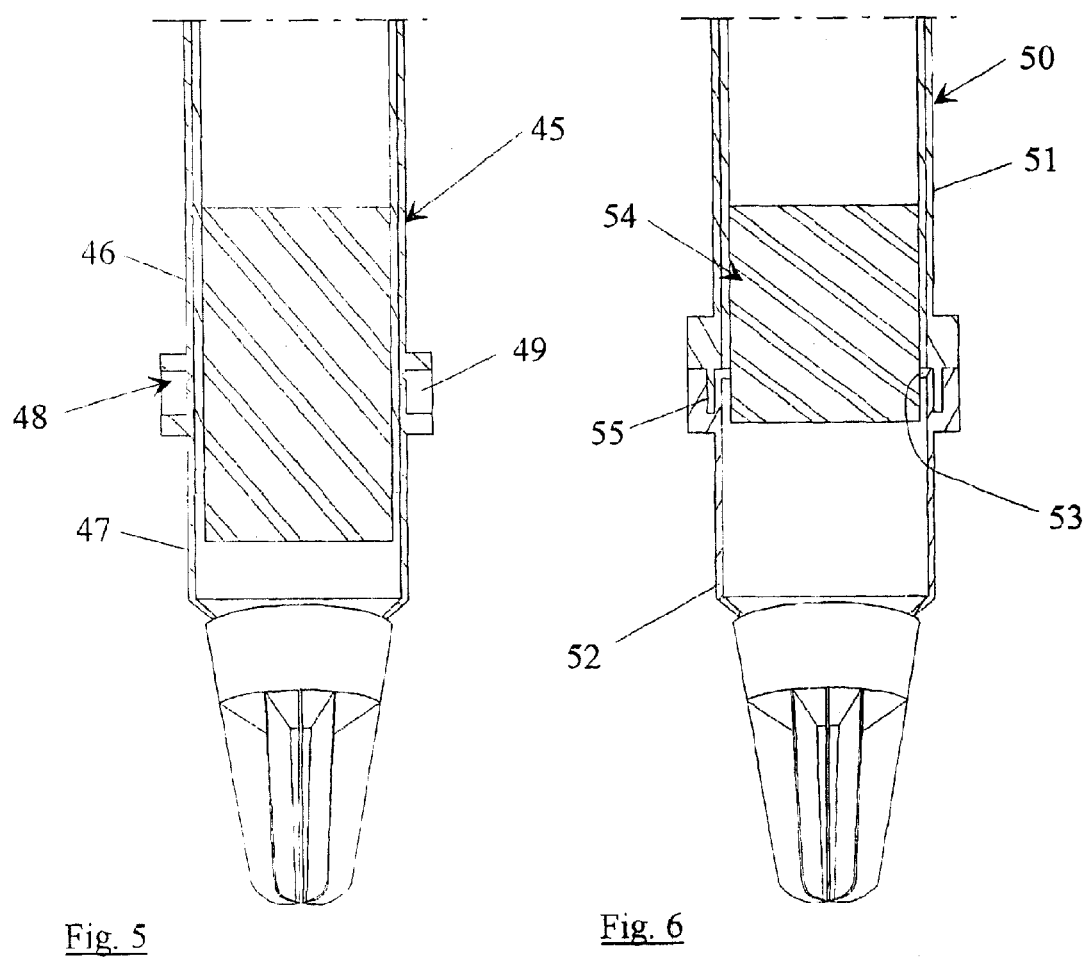

SAMPLE CYLINDER, ESPECIALLY A SAMPLE CYLINDER THAT IS PROVIDED WITH A FILTRATION DEVICE FOR RECOVERING CELL MATERIAL FROM BODY FLUIDS

PRIORITY CLAIM

This is a U.S. national stage of application No. PCT/DE01/01839, filed on 16May 2001. Priority is claimed on that application and on the following application: Country: Germany, Application No.: 100 24 137.9, Filed: 18 May 2000.

BACKGROUND OF THE INVENTION

1. Field of the Invention

The invention is directed to a sample cylinder or specimen cylinder with a syringe cone segment, particularly with a filtering device for recovering cell material from body fluids.

2. Description of the Related Art

A filtering device for separating and collecting cells and particles from liquids is known from DE 3719302, which corresponds to U.S. Pat. No. 4,973,450. Efficiency can be increased through the use of this device, particularly in quantitative evaluation methods, e.g., in urine sediment analysis. The device described in the above-cited reference has a specimen cylinder with a syringe cone segment. A filtration tube which is displaceable in the manner of a syringe plunger and has a one-stage or two-stage filter device at one end is inserted into the specimen vessel.

Diagnostic chores, e.g., in the field of urine analysis, require that the particles occurring in urine, such as erythrocytes, leukocytes, urothelial cells, other accompanying cells, crystalline bodies, hyaline cylinders and germs are concentrated and accumulated from a large quantity of liquid, e.g., from a full bladder or from 50-ml or 100-ml samples, without losses in a sediment or in a constant 1-ml amount of liquid. This allows the filtering device to separate and collect cells and particles from liquids, e.g., from urine. Qualitative evaluation is carried out in a manner known per se by adding the specimen by drops to cell counters.

In connection with improved diagnostic possibilities, the known device was improved for cytological purposes where the cell material on microscope slides should have a perfect morphology. To this end, a filtration tube in a known device is guided inside a specimen cylinder with a syringe cone segment and adjoining cylinder segment so as to be sealed against the cylindrical inner wall of the specimen cylinder. When a liquid is drawn in the manner of a syringe and received in the specimen cylinder, and the syringe cone is closed or the specimen cylinder, with the filtration tube removed, is filled with body fluid and then the filtration tube is inserted, the specimen liquid passes through the filtering device when the filtration tube is pressed down against the specimen liquid and collects in the filtration tube or passes out in some other manner.

During the filtration process, additional particles collect on a filter surface which projects particularly over the filtering device. The filtration tube is then usually removed from the specimen cylinder after the specimen liquid has been withdrawn. The particles which have collected on the filter surface can then be transferred to a slide, e.g., for microscopic diagnosis, so that an accumulated suspension in the specimen cylinder which is needed for quantitative analysis is dispensed with.

This print technique has proven extremely successful for obtaining medical preparations. However, in order to transfer the cell material that has collected on the filter surface to slides by this kind of printing, the filtration tube must be removed from the specimen cylinder. For this purpose, after the filtrate or residue has been removed, the device which is now open is turned over and set on a cellulose base, for example. The specimen cylinder can then be pulled out of the filtration tube against considerable resistance through the use of corresponding force. In so doing, remainders of the specimen will inevitably flow down the outer wall and can wet the user's fingers as well as the base. This risk of contamination, for example, in case of infectious material, is disadvantageous and is not tolerable for reasons of hygiene.

Precisely in view of such a risk of contamination, reuse of devices that have already been used should also be ruled out.

SUMMARY OF TILE INVENTION

This set of technical problems is solved generally in a specimen cylinder with a syringe cone segment by the specimen cylinder according to the invention, wherein the syringe cone segment can be separated from a cylinder segment. In particular, the idea consists in that in a specimen cylinder having a filtering device with a filter which is held so as to be sealed relative to the inner wall of the specimen cylinder, a surface of the filter projects axially over its holder and over the cylinder segment in an operational position of the filtering device when the syringe cone segment is removed.

The steps undertaken in the specimen cylinder according to the invention achieve a number of advantages. When the filtering device is inserted into the specimen cylinder in the manner of a filtering tube, it no longer needs to be removed from the specimen cylinder. Rather, the filter surface with the collected cell contents and particles is freely accessible after the syringe cone segment is removed, for example, for transferring these cell contents and particles onto a microscope slide or specimen carrier. For this purpose, the surface advisably projects axially over the holder of the filter as well as over the cylinder segment in this operational position and is accordingly freely accessible.

Consequently, the cell material that has collected on the surface of the filter comes into contact with the environment when and only when it also undergoes further preparation. In particular, an unintentional drying out of the filter outside of the specimen cylinder is also impossible. Rather, the filter surface with the cell material remains in the microclimate of the specimen cylinder until the above-mentioned preparation step. Also, a mechanical influence on the cell contents on the filter surface, e.g., due to tilting of the filtering device during removal, striking against the free edge of the specimen cylinder or the like, is reliably prevented by the steps according to the invention.

In a preferred construction, the cylinder segment and a portion of the syringe cone segment form a common cylindrical inner wall of the specimen cylinder. The syringe cone is accordingly completely severed from the cylinder segment, i.e., separation is effected in an area having a constant, cylindrical cross section and not in the area of the syringe cone tapering toward the free end. As a result of this step, the maximum cross section of the specimen cylinder is available at the separation point after the syringe cone segment is severed. Further, the axial movability of the inserted filtering device can not be impaired in any way by this step. Moreover, the tightness of the holder relative to the inner wall of the specimen cylinder is ensured, even up to the separating point, because there is no change in cross section in the inner wall.

In a first alternative design, the cylinder segment and syringe cone segment are constructed in two pieces. Suitable steps must then be taken to connect the syringe cone segment to the cylinder segment so as to be tight against liquid.

When an axially stationary filtering device is desired, the holder of the filter can connect the cylinder segment and syringe cone segment to one another. A connection of this kind can be provided in a manner known per se by suitable snap-in connections, catch connections and screw connections. Sealing rings which guarantee a liquid-tight connection can be provided in addition.

However, since axial movability of the filtering device is usually necessary for the tasks mentioned in the beginning, the cylinder segment and syringe cone segment are advisably connected to one another by an outer and/or inner sleeve. With respect to an outer sleeve, the cylinder segment and syringe cone segment advisably have the same outer and preferably the same inner diameter at least in the area of the separation point. For an inner sleeve, identical inner diameters are also usually required. When the inner sleeve extends over the entire cylindrical area of the specimen cylinder, there is also no problem with sealing relative to the holder for the filter. Alternatively, a front side of an inner sleeve of this type can form a deliberate axial stop for the filtering device, e.g., for fixing an exact volume of the syringe cone segment.

Also, different inner diameters of the cylinder segment and syringe cone segment can be compensated by an inner sleeve with a stepped or graduated outer diameter and an inner diameter can be made available specifically for filtering devices that are adapted for special tasks.

It is possible to construct the sleeves separately. Alternatively, a sleeve of this type can also be constructed integral with the cylinder segment and/or with the syringe cone segment such that the cylinder segment and syringe cone segment are connected so as to overlap axially. In individual cases, a telescoping insertion of the cylinder segment and syringe cone segment may also be adequate as a connection.

Besides the two-piece constructional variant, the cylinder segment and syringe cone segment can also be constructed in one piece and can be separable at a predetermined breaking point. In this variant also, separation is possible in a well-defined manner by means of the predetermined breaking point. A predetermined breaking point of this kind is usually formed at this location by a narrowing of the cross section and, if required, can be mechanically reinforced by ribs which break or tear in a suitable manner.

Regardless of whether a one-piece or two-piece construction is carried out, it is provided in a further development that the connection of the syringe cone segment to the cylinder segment is carried out in the manner of a safety lock or tamperproof closure such as is known in the art, e.g., for bottles. This step makes it possible to detect used equipment in a reliable manner regardless of whether or not the specimen cylinder according to the invention can regularly be separated into cylinder segment and syringe cone segment and then assembled again.

In exceptional cases, particularly for applications requiring highly sterile conditions, the latter feature is usually undesirable. In that case, it is provided that when the connection elements and/or sealing elements or the syringe cone segment itself are destroyed when the syringe cone segment is severed from the cylinder segment, they can not be put together again so as to be operational.

It can be provided particularly in the two-piece construction of the specimen cylinder according to the invention that the specimen cylinder has an axial stop for the filtering device in the area of the separation point of the syringe cone segment and cylinder segment. In particular, the severed edges of the syringe cone segment and cylinder segment can have, as a stop, a projection which faces inward and projects over the inner wall. This step also ensures that a defined, predeterminable volume is available on the syringe cone side.

The invention will be described more fully with reference to the drawings which show embodiment examples only.

BRIEF DESCRIPTION OF THE DRAWINGS

FIG. 1 is a sectional view showing a specimen cylinder with inserted filtering device according to the invention;

FIG. 2 shows the specimen cylinder according to FIG. 1 without the syringe cone segment;

FIG. 5 shows a fourth embodiment example; and

FIG. 6 shows a fifth embodiment example.

DETAILED DESCRIPTION OF THE PRESENTLY PREFERRED EMBODIMENTS

Figures 3, 4:
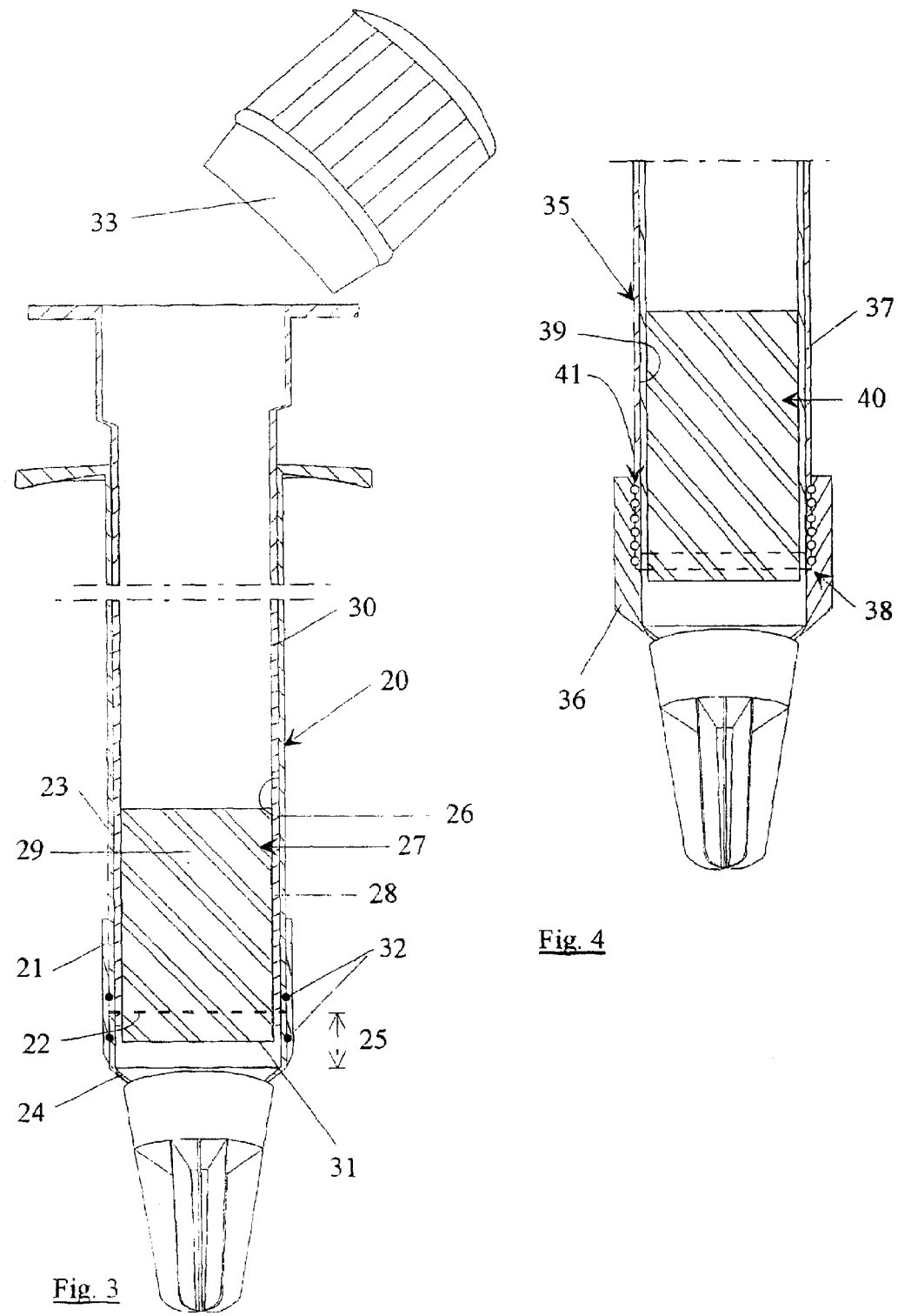
FIG. 3 shows a second embodiment example in section in the area of the separation point.
FIG. 4 shows a third embodiment example.

FIG. 1 shows a specimen cylinder 1, according to the invention, comprising a cylinder segment 2 and a separable syringe cone segment 3 which are constructed in two pieces in the embodiment example shown in FIGS. 1 and 2. The syringe cone segment 3 which is closed by a cap 4 is connected to the cylinder segment 2 by a holder 5 of a filtering device 6, shown in a simplified manner, which is inserted into the specimen cylinder 1 and which is also already known, e.g., from DE 3719302. The holder 5 holds a filter 8 by a portion 11 so as to be sealed relative to the inner wall 7 of the specimen cylinder 1. The filter 8 projects axially over the holder 5 by a surface 9. This projecting portion has a mushroom-like appearance owing to a radial necking down of the filter 8 due to the holder 5, e.g., due to a conical filter receptacle and a circumferential projection which faces radially inward.

The cylinder segment 2 and a portion 10 of the syringe cone segment 3 together form the cylindrical inner wall 7 of the specimen cylinder 1. Consequently, the holder 5 can join the cylinder segment 2 and the syringe cone segment 3 together by portion 11 which has a constant cross section formed by the dimensioning of the inner cylindrical area of the specimen cylinder 1.

Depending on the construction, this connection can be carried out by means of a simple press fit and/or clamping fit of the cylinder segment 2 and syringe cone segment 3 on portion 11 of the holder 5. Catch closures, snap-in closures or screw closures, not shown in particular, are all equally possible without difficulty. Further, sealing elements such as sealing rings 14 can be inserted in portion 11 in addition. These steps are essentially determined by the intended use of the specimen cylinder 1 according to the invention.

In the embodiment form shown in FIGS. 1 and 2, the filtering device 6 is not inherently axially displaceable in the specimen cylinder 1. Nevertheless, a liquid specimen can easily be sucked in by drawing out the tube 15. Alternatively, for example, a suction pump, a balloon 17 of sufficient size, or the like, can be fitted to the free end 13 of the specimen cylinder 1. As a result of the liquid flowing through the filter 8 in the direction indicated by the arrow 12, cell material that is filtered out is deposited on the surface 9 of the filter 8.

After the collected liquid has been removed, possibly after removing the cap 4, including the liquid collected in the syringe cone segment 3, the syringe cone segment 3 can be severed from the cylinder segment 2, according to the invention, in the plane 17 indicated by a dash-dot line in FIG. 1. In the operational position of the filtering device 6 according to FIG. 2, the surface 9 then projects freely axially over the cylinder segment 2 and the holder 5.

In this embodiment example, the cylinder segment 2 and the holder 5 of the filtering device 6 can be nondetachably connected and, if necessary, can even be constructed so as to form one piece.

In order to place a medical preparation on a microscope slide or specimen carrier 16, the cylinder segment 2 with the filtering device 6 is carefully placed by its surface 9 on the specimen carrier vertically as indicated by arrow 18 in FIG. 2 in order to transfer the cell material located on the surface 9 to the specimen carrier 16.

When a cylindrical portion 25 of the syringe cone segment 24 and the cylinder segment 23 have the same inner cross section as is shown in FIG. 3, a common inner wall 26 of the specimen cylinder 20 is formed. Accordingly, the filtering device 27 can move freely axially. A tube 30 which is guided within the specimen cylinder 20 and sealed relative to the latter forms a holder 28 of the filter 29 at the same time. Then a specimen liquid which is drawn in when the cap 33 is attached collects in the tube 30.

When a filtering process is concluded, the filtrate located in the tube 30 can be poured off, according to the prior art, the tube 30 can be removed from the specimen cylinder 20 in the manner described above, and the cell material located on the filter surface 31 can be transferred to a specimen carrier. Filtrate still remaining in the tube can serve as a backwash medium if required.

However, in the specimen cylinder according to the invention, the tube 30 is restored to the position shown in FIG. 3 after the filtrate has been poured off, and the filter surface 24 projects axially over the holder 28 of the filter 29 and over the cylinder segment 23 after the syringe cone segment 24 has been removed for transferring the filtered out cell material to a specimen carrier.

For this purpose, in the two-piece embodiment form of the specimen cylinder 20 according to FIG. 3, an outer sleeve 21 overlaps a separation 22, shown in an enlarged view, between the cylinder segment 23 and the syringe cone segment 24.

In a simple embodiment form, the outer sleeve 21 which is constructed as a shrink tubing, for example, can connect the cylinder segment 23 to the syringe cone segment 24. However, solidly constructed sleeves 21 which are formed in such a way that the syringe cone segment 24 and the cylinder segment 23 are connected with the sleeve 21 by means of a catch connection, a snap connection or screw connection, possibly including suitable sealing elements, are preferable.

Further, separately constructed sealing rings 32 are additionally provided so that the holder 28 for the filter 29 of the filtering device 27 is well-sealed relative to the inner wall 26.

In the specimen cylinder 35 according to FIG. 4, which is also a two-part construction, the syringe cone segment 36 is constructed in the manner of a cap so as to axially overlap and engage over the cylinder segment 37. It can be ensured by means of suitable graduation (see arrow 38) that a portion of the cylinder segment 36 and the cylinder segment 37 form a common cylindrical inner wall 39. Due to this step, the filtering device 40 is again freely movable axially within the specimen cylinder 35.

Arrow 41 indicates the connection elements and/or sealing elements which ensure the liquid-tight connection of the syringe cone segment 36 to the cylinder segment 37. For example, these elements can be inserted sealing rings, suitably constructed projections and recesses which catch or snap together, a thread, or the like.

When it must be ensured in particular that the specimen cylinder according to the invention can not be reused, these connection elements and/or sealing elements 41 are advisably destroyed when the syringe cone segment 36 is detached from the cylinder segment 37 in such a way that it is no longer possible to reassemble them so as to be operational.

Accordingly, a connection between the syringe cone segment 36 and the cylinder segment 37 is constructed in the manner of a tamperproof closure which allows reliable detection of tampering.

In addition to the two-piece construction of the specimen cylinder according to the invention, it is also possible to construct a specimen cylinder 45 in one piece in a simple manner with respect to manufacturing technique. The cylinder segment 46 and syringe cone segment 47 can then be separated in a regular manner at a predetermined breaking point 48 with a clearly defined area of separation. A predetermined breaking point 48 of this kind usually has a cross section which is small enough to enable the cylinder segment 45 and syringe cone segment 47 to be separated easily by tearing or breaking the predetermined breaking point 48. In order to ensure sufficient mechanical stability, reinforcing ribs 49, which are also provided with predetermined breaking points themselves if need be, can further strengthen the mechanically weak connection along the predetermined breaking point 48.

In a one-part construction of this kind, the specimen cylinder 45 can also be designed so as to be reusable. Alternatively, it is also possible in this case to exclude reuse by appropriate tearing or breaking of the predetermined breaking point 48 and/or ribs 49. In every case, in a one-piece construction of the specimen cylinder 45 of this type, it can easily be seen whether or not it has already been used.

FIG. 6 shows another two-part construction of a specimen cylinder 50 with a cylinder segment 51 and a syringe cone segment 52. In the two-part embodiment form shown in FIG. 6, it is possible to provide the ends of the cylinder segment 51 and syringe cone segment 52 that face one another with a projection 53 which faces radially inward.

When projections of the type mentioned above are provided at the syringe cone segment 52 as well as at the cylinder segment 51, they can also be used as a connection element and/or sealing element. In particular, a projection 53 of this kind which projects inward also forms an axial stop for the filtering device 54. Accordingly, an exactly defined volume can be predetermined inside the syringe cone segment 52 in the operational position of the filtering device 54 according to FIG. 6. When the wall of the cylindrical portion of the syringe cone segment 52 is constructed with a suitable thickness, its front side can also form the stop for the filtering device 54 without the need for a projection 53 projecting over the inner wall.

Further, FIG. 6 shows a radially circumferential, axially projecting lip 55 at the end of the cylinder segment 50 facing the syringe cone segment 52. This lip 55 is held in a sealing manner in a corresponding recess of the syringe cone segment 52. In this case, also, the abovementioned steps for additional sealing and for a secure hold can again be provided in the form of sealing elements, snap-in and catch connections, threads, etc.

What is claimed is:

1. A specimen cylinder comprising:
   a cylinder segment having a circumferential inner wall;
   a syringe cone segment integrally formed with the cylinder segment so that the cylinder segment and the syringe cone segment form a one-piece element having a frangible structure forming a predetermined breaking point, wherein the one-piece element can be severed at the predetermined breaking point to separate said syringe cone segment from said cylinder segment, said syringe cone segment having an inner wall; and a filtering device held in said cylinder segment and sealed relative to said inner wall of said cylinder segment, said filtering device comprising a filter and a holder which holds the filter so that an axial end surface of the filter is covered by said syringe cone segment when said syringe cone segment is connected to said cylinder segment and said axial end surface projects axially beyond said holder and beyond said cylinder segment after said syringe cone segment is separated from said cylinder segment.

2. The specimen cylinder of claim 1, wherein before said syringe cone segment is separated from said cylinder segment, said inner wall of said cylinder segment and said inner wall of said syringe cone segment form a common cylindrical inner wall of said specimen cylinder.

3. The specimen cylinder of claim 1, wherein said cylinder segment and said syringe cone segment can be separated without damaging the specimen cylinder.

4. The specimen cylinder of claim 1, further comprising a tamperproof closure where said cylinder segment and said syringe cone segment can be separated.

5. The specimen cylinder of claim 1, further comprising means for rendering the specimen cylinder inoperable when said syringe cone segment is separated from said cylinder segment.

6. The specimen cylinder of claim 1, wherein said cylinder segment comprises an axial stop for positioning said filtering device.

7. The specimen cylinder of claim 1, wherein the axial end surface of the filter is shaped so as to be suitable for being pressed onto a specimen slide.

8. A specimen cylinder comprising:

a cylinder segment having an inner wall;

a syringe cone segment integrally formed with the cylinder segment so that the cylinder segment and the syringe cone segment form a one-piece element having a frangible structure forming a predetermined breaking point, wherein the one-piece element can be severed at the predetermined breaking point to separate said syringe cone segment from said cylinder segment; and a filtering device held in the cylinder segment and comprising a filter and a holder, the holder having an outer radial surface which sealingly engages the inner wall of the cylinder segment and an inner radial surface which holds the filter, the filter having an axial end surface which is covered by the syringe cone segment when the syringe cone segment is connected to the cylinder segment and which, after the syringe cone segment is separated from the cylinder segment, projects axially beyond the holder and beyond the cylinder segment.

9. The specimen cylinder of claim 1, wherein said cylinder segment has a proximate end and a distal end, said predetermined breaking point being arranged at said distal end, said axial end surface of said filter projecting outward from said distal end after said syringe cone segment is separated from said cylinder segment.

10. The specimen cylinder of claim 8, wherein said cylinder segment has a proximate end and a distal end, said predetermined breaking point being arranged at said distal end, said axial end surface of said filter projecting outward from said distal end after said syringe cone segment is separated from said cylinder segment.

11. The specimen cylinder of claim 1, wherein said filtering device is arranged so that a filtrate can be drawn through said filter into a space defined by said inner wall of said cylinder segment and said filtering device.

* * * * *